(12) United States Patent
Hansenne et al.

(10) Patent No.: US 6,436,376 B1
(45) Date of Patent: Aug. 20, 2002

(54) ENHANCED SPF UV-SUNSCREEN/TRICONTANYL PVP PHOTOPROTECTING (SPRAYABLE) FORMULATIONS

(75) Inventors: Isabelle Hansenne, Westfield; Donald W. Rick, Dumont, both of NJ (US)

(73) Assignee: Societe L'Oreal S.A., Paris (FR)

( * ) Notice: Subject to any disclaimer, the term of this patent is extended or adjusted under 35 U.S.C. 154(b) by 0 days.

(21) Appl. No.: 09/791,603

(22) Filed: Feb. 26, 2001

(51) Int. Cl.$^7$ .............. A61K 7/42; A61K 7/44; A61K 7/00; A61K 31/74
(52) U.S. Cl. .......... 424/59; 424/60; 424/78.02; 424/78.08; 424/400; 424/401
(58) Field of Search .......... 424/59, 60, 78.02, 424/78.08, 400, 401

(56) References Cited

U.S. PATENT DOCUMENTS

| | | |
|---|---|---|
| 4,642,267 A | 2/1987 | Creasy et al. |
| 4,769,013 A | 9/1988 | Lorenz et al. |
| 5,518,712 A | 5/1996 | Stewart |
| 5,885,557 A | 3/1999 | Lentini |
| 5,916,541 A | 6/1999 | Stweart |
| 6,074,630 A * | 6/2000 | Devillez et al. .......... 424/59 |

FOREIGN PATENT DOCUMENTS

| | | |
|---|---|---|
| EP | 0 819 428 A2 | 1/1998 |
| WO | WO 97/42933 | 11/1997 |
| WO | WO 00/41672 | 7/2000 |

OTHER PUBLICATIONS

Gupta et al., "In vitro method for modeling water resistance of sunscreen formulations", J. Cosmet. Sci., 50, 79–90, Mar./Apr. 1999).

* cited by examiner

Primary Examiner—Shelley A. Dodson
(74) Attorney, Agent, or Firm—Burns, Doane, Swecker & Mathis, L.L.P.

(57) ABSTRACT

Topically applicable cosmetic/dermatological compositions well suited for both effective and SPF-enhanced UV-photoprotection of human skin, hair and/or scalp, most preferably packaged as spray delivery systems, contain (a) an effective UV-photoprotecting amount of at least one UV-A and/or UV-B sunscreen, most notably the sunscreen avobenzone, and (b) an amount of the copolymer tricontanyl PVP effective to statistically significantly enhance the SPF value of said at least one UV-A and/or UV-B or avobenzone sunscreen, formulated into (c) a topically applicable, cosmetically/dermatologically acceptable vehicle, diluent or carrier therefor; the subject compositions optionally contain a thus-effective amount of an artificial/sunless tanning agent.

32 Claims, No Drawings

ENHANCED SPF UV-SUNSCREEN/TRICONTANYL PVP PHOTOPROTECTING (SPRAYABLE) FORMULATIONS

CROSS-REFERENCE TO COMPANION APPLICATION

Copending application Ser. No. 09/791,734, filed concurrently herewith and assigned to the assignee hereof.

BACKGROUND OF THE INVENTION

1. Technical Field of the Invention

The present invention relates to novel cosmetic/dermatological compositions for topical application, most notably sprayable formulations, for the ultraviolet (UV)-photoprotection of the skin and/or the hair against the damaging effects of UV radiation, in particular solar radiation, and to the use of same for the cosmetic/dermatological applications indicated above.

This invention more especially relates to topically applicable, enhanced SPF UV-A and/or UV-B sunscreen/tricontanyl PVP photoprotecting compositions, particularly sprayable formulations, advantageously comprising the sunscreen avobenzone and also comprising a sunless or artificial tanning agent such as dihydroxyacetone ("DHA").

2. Description of the Prior Art

It is well known to this art that light radiation of wavelengths of from 280 nm to 400 nm promotes tanning of the human epidermis, and that irradiation of wavelengths of from 280 to 320 nm, i.e., UV-B irradiation, causes erythema and burning of the skin which can impair the development of a natural tan; hence, such UV-B radiation must thus be screened from the skin.

It is also known to this art that UV-A radiation, of wavelengths from 320 to 400 nm, which tans the skin, also adversely affects it, in particular in the case of sensitive skin or a skin which is continually exposed to solar radiation.

UV-A rays cause, in particular, a loss in the elasticity of the skin and the appearance of wrinkles, promoting a premature aging thereof. Such irradiation promotes triggering of the erythematous reaction or enhances this reaction in certain individuals, and may even be the source of phototoxic or photoallergic reactions. Thus, it is desirable to also screen out UV-A radiation.

A wide variety of cosmetic compositions intended for the photoprotection (UV-A and/or UV-B) of human skin is known to this art.

These photoprotective/sunscreen compositions are quite often oil-in-water emulsions (namely, a cosmetically acceptable vehicle, carrier or diluent comprising an aqueous continuous dispersing phase and an oily discontinuous dispersed phase) which contains, in various concentrations, one or more standard lipophilic and/or hydrophilic organic sunscreen compounds capable of selectively absorbing harmful or deleterious UV radiation. These sunscreen compounds (and the amounts thereof) are selected as a function of the desired sun protection factor (the sun protection factor (SPF) being expressed mathematically by the ratio of the irradiation time required to attain the erythema-forming threshold with the UV screening agent to the time required to attain the erythema-forming threshold in the absence of UV screening agent).

Too, there exists an increasing demand for higher SPF suncare products, particularly high SPF sunscreen sprays. High SPFs can be attained by incorporating more sunscreens at elevated levels; however, this is not always feasible, as sunscreens add considerable cost to the formulation and high sunscreen levels can promote increased irritancy.

Corollary thereto, the dibenzoylmethane sunscreen avobenzone, for example, is a particularly attractive chemical UV-absorber/filter. But it is even more difficult to formulate high SPF sunscreen products when the formulation contains avobenzone, as it is incompatible with many other sunscreen filters (for example, formulations with octyl methoxy cinnamate are generally not photostable).

Much more difficult is the formulation of high SPF avobenzone sprayable compositions. Indeed, high SPF sunscreen sprays are commercially available, but these do not contain avobenzone. Typically, high SPF values are obtained by formulating high levels of UV-B absorbing sunscreens, such as octylmethoxy cinnamate. Nonetheless, these formulations provide no protection against longer wavelength UV-A irradiation.

Also representative of the state of the prior art are:

U.S. Pat. Nos. 5,518,712 and 5,916,541 to Stewart and his WO 97/42933, describing sunscreen protection and insect repellent combination compositions purportedly providing SPF factors of about 2 to about 50. These include a sunscreen agent, whatever its chemical/physical structure and variously oxybenzone or benzophenone-3, an insect repellent, an emulsifing agent and a film former, all in an aqueous solvent. These compositions are said to form a thin film on the skin, but are non-greasy to the touch and are easily removed by scrubbing with soap and water. The film former is also said to add waterproofing properties to be subject compositions and one, of many, examples of which is poly(vinyl pyrrolidone/1-triacontene (tricontanyl PVP)).

U.S. Pat. No. 6,074,630 to Devillez et al., relating to delivery systems for sunscreen products that apply a dry, waterproof sunscreen composition to the skin. The sunscreen composition is applied to an article such as paper, nonwoven cloth or porous plastic which is subsequently rubbed onto the skin. Or, the sunscreen may take the form of a wafer or a bar with or without a support article. Among the list of FDA-approved sunscreen agents suitable according to this particular invention is oxybenzone, and, in general, the patented sunscreen products may contain PVP/hexadecene copolymer or other waterproofing agent, e.g., tricontanyl PVP.

Tricontanyl PVP (Ganex WP-660) also appears in Table 1 of U.S. Pat. No. 5,885,557 to Lentini, relating to compositions useful in the phototherapeutic treatment of psoriasis and other proliferative skin diseases. Such compositions comprise dihydroxyacetone and a penetration attenuator, both in a cosmetically and/or pharmaceutically acceptable carrier. The subject compositions are said to be useful in the exploitation during phototherapeutic treatment of the hyperdesquamation characteristics of the psoriatic or otherwise affected skin.

WO 00/41672 also features a combined insect repellent and sunscreen composition, including one or more inorganic sunscreening agents, but which may also include one or more other UV sunscreening agents, generally organic compounds such as oxybenzone or Parsol MCX and, optionally, a film former, preferably tricontanyl PVP.

Cf. EP 0 819 428 A2, assigned to the assignee hereof, and Gupta and Zatz, *J. Cosmet. Sci.*, 50, 79–90 (March/April 1999), "In Vitro Method for Modeling Water Resistance of Sunscreen Formulations," describing formulating two of the most frequently used sunscreens, benzophenone-3 and octyl methoxycinnamate (OMC) into hydroalcoholic, diisopropyl adipate oil prototype compositions and o/w and w/o emulsions. An in vitro procedure was thus developed for measuring the water resistance of sunscreens and assessing their ability to resist washoff.

SUMMARY OF THE INVENTION

It has now unexpectedly and surprisingly been determined that statistically significant, markedly enhanced SPF values can be attained by formulating an effective UV-photoprotecting amount of at least one UV-A and/or UV-B sunscreen, in particular the sunscreen filter avobenzone, with the particular polymeric film former tricontanyl PVP.

It has even more unexpectedly and surprisingly been determined that high SPF sunscreen sprays are provided by formulating UV-A and/or UV-B sunscreen/tricontanyl PVP sprayable compositions; this because of the art-recognized difficulty of achieving high SPF values in sprayable formulations.

Enhanced SPF values have also now been obtained for artificial tanning, or sunless tanning sprays containing UV-A and/or UV-B sunscreens, for example artificial/sunless tanning sprays also containing the artificial tanning agent, dihydroxyacetone ("DHA").

DETAILED DESCRIPTION OF BEST MODE AND SPECIFIC/PREFERRED EMBODIMENTS OF THE INVENTION

More particularly according to the present invention, the subject compositions contain (a) an effective UV-photoprotecting amount of at least one UV-A and/or UV-B sunscreen and (b) an amount of the copolymer tricontanyl PVP effective to statistically significantly enhance the SPF value of said at least one UV-A and/or UV-B sunscreen, formulated into (c) a topically applicable, cosmetically/dermatologically acceptable vehicle, diluent or carrier therefor.

By "UV-A and/or UV-B sunscreen" is intended any compound or any combination of compounds which, by mechanisms that are known per se of absorption and/or reflection and/or scattering of UV-A and/or UV-B radiation, prevents, or at least limits, the contact between such radiation and a surface (skin, hair) on which this or these compounds have been applied. Stated differently, these compounds may be UV-absorbing organic screening agents or inorganic (nano) pigments which scatter and/or reflect UV radiation, as well as mixtures thereof.

According to the present invention, the at least one UV-A and/or UV-B sunscreen may comprise one or more hydrophilic organic screening agents and/or one or more lipophilic organic screening agents and/or one or more mineral or inorganic (nano)pigments.

The most preferred UV-photoprotecting agent according to the present invention is the dibenzoylmethane sunscreen avobenzone, or 4-(tert-butyl)-4'-methoxydibenzoylmethane, which is very well known to this art, is commercially available and is marketed, for example, under the trademark "PARSOL 1789" by Givaudan. It has the structural formula:

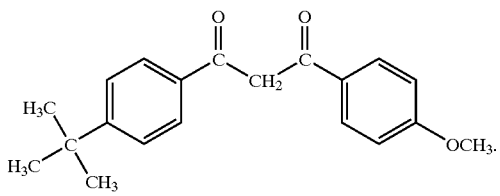

Sunscreens according to the present invention which are physical blockers reflect or scatter ultraviolet radiation. Typical examples of physical blockers include red petrolatum, titanium dioxide, and zinc oxide. These physical blockers have been employed in a variety of suspensions and particle sizes and are frequently included in cosmetic formulations. A review of physical blockers may be found at "Sun Protection Effect of Nonorganic Materials," by S. Nakada & H. Konishi, *Fragrance Journal*, Volume 15, pages 64–70 (1987), which is incorporated by reference herein.

Sunscreens according to this invention which are chemical absorbers, like avobenzone, actually absorb harmful ultraviolet radiation. It is well known that chemical absorbers are classified, depending on the type of radiation they protect against, as either UV-A or UV-B absorbers. UV-A absorbers generally absorb radiation in the 320 to 400 nm region of the ultraviolet spectrum. UV-A absorbers include anthranilates, benzophenones, and dibenzoyl methanes. UV-B absorbers generally absorb radiation in the 280 to 320 nm region of the ultraviolet spectrum. UV-B absorbers include p-aminobenzoic acid derivatives, camphor derivatives, cinnamates, and salicylates.

Classifying the chemical absorbers generally as UV-A or UV-B absorbers is accepted within the industry. However, a more precise classification is one based upon the chemical properties of the sunscreens. There are eight major classifications of sunscreen chemical properties which are discussed at length in "Sunscreens—Development, Evaluation and Regulatory Aspects," by N. Shaath et al., 2nd. Edition, pages 269–273, Marcel Dekker, Inc. (1997). This discussion, in its entirety, is incorporated by reference herein.

The sunscreens which may be formulated according to the present invention typically comprise chemical absorbers, but may also comprise physical blockers. Exemplary sunscreens which may be formulated into the compositions of the present invention are chemical absorbers such as p-aminobenzoic acid derivatives, anthranilates, benzophenones, camphor derivatives, cinnamic derivatives, dibenzoyl methanes, β,β-diphenylacrylate derivatives, salicylic derivatives, triazine derivatives, benzimidazole compounds, bis-benzoazolyl derivatives, methylene bis-(hydroxyphenylbenzotriazole) compounds, the sunscreen polymers and silicones, or mixtures thereof. These are variously described in U.S. Pat. Nos. 2,463,264, 4,367,390, 5,166,355 and 5,237,071 and in EP-0,863,145, EP-0,517, 104, EP-0,570,838, EP-0,796,851, EP-0,775,698, EP-0,878, 469, EP-0,933,376, EP-0,893,119, EP-0,669,323, GB-2,303, 549, DE-1,972,184 and WO-93/04665, also expressly incorporated by reference. Also exemplary of the sunscreens which may be formulated into the compositions of this invention are physical blockers such as cerium oxides, chromium oxides, cobalt oxides, iron oxides, red petrolatum, silicone-treated titanium dioxide, titanium dioxide, zinc oxide, and/or zirconium oxide, or mixtures thereof.

A wide variety of sunscreens is described in U.S. Pat. No. 5,087,445, issued to Haffey et al. on Feb. 11, 1992; U.S. Pat.

No. 5,073,372, issued to Turner et al. on Dec. 17, 1991; and Chapter VIII of *Cosmetics and Science and Technology* by Segarin et al., pages 189 et seq. (1957), all of which are incorporated herein by reference in their entirety.

Preferred among those sunscreens which may be formulated into the compositions of the instant invention are those selected from among: aminobenzoic acid, amyldimethyl PABA, cinoxate, diethanolamine p-methoxycinnamate, digalloyl trioleate, dioxybenzone, 2-ethoxyethyl p-methoxycinnamate, ethyl 4-bis(hydroxypropyl) aminobenzoate, 2-ethylhexyl-2-cyano-3,3-diphenylacrylate, ethylhexyl p-methoxycinnamate, 2-ethylhexyl salicylate, glyceryl aminobenzoate, homomenthyl salicylate, homosalate, 3-imidazol-4-ylacrylic acid and ethyl ester, methyl anthranilate, octyldimethyl PABA, 2-phenylbenzimidazole-5-sulfonic acid and salts, red petrolatum, sulisobenzone, titanium dioxide, triethanolamine salicylate, N, N, N-trimethyl-4-(2-oxoborn-3-ylidene methyl)anillinium methyl sulfate, and mixtures thereof.

Similarly preferred sunscreens active in the UV-A and/or UV-B range include:

p-aminobenzoic acid, oxyethylene (25 mol) p-aminobenzoate, 2-ethylhexyl p-dimethylaminobenzoate, ethyl N-oxypropylene p-aminobenzoate, glycerol p-aminobenzoate, 4-isopropylbenzyl salicylate, 2-ethylhexyl 4-methoxycinnamate, methyl diisopropylcinnamate, isoamyl 4-methoxycinnamate, diethanolamine 4-methoxycinnamate, 3-(4'-trimethylammunium)-benzyliden-bornan-2-one methylsulfate, 2-hydroxy-4-methoxybenzophenone, 2-hydroxy-4-methoxybenzophenone-5-sulfonate, 2,4-dihydroxybenzophenone, 2,2',4,4'-tetrahydroxybenzophenone, 2,2'-dihydroxy-4,4'dimethoxybenzophenone, 2-hydroxy-4-n-octoxybenzophenone, 2-hydroxy-4-methoxy-4'-methoxybenzophenone, β(2-oxoborn-3-ylidene)-tolyl-4-sulfonic acid and soluble salts thereof, 3-(4'-sulfo)benzyliden-bornan-2-one and soluble salts thereof, 3-(4'methylbenzylidene)-d,1-camphor, 3- benzylidene-d,1-camphor, benzene 1,4-di(3-methylidene-10-camphosulfonic) acid and salts thereof (the product Mexoryl SX described in U.S. Pat. No. 4,585,597 issued to Lange et al. on Apr. 29, 1986), urocanic acid, 2,4,6-tris[p-(2'-ethylhexyl-1'-oxycarbonyl)-anilino]-1,3,5-triazine, 2-[(p-(tertiobutylamido)anilino]-4,6-bis-[(p-(2'-ethylhexyl-1'-oxycarbonyl)anilino]-1,3,5-triazine, 2,4-bis{[4-(2-ethyl-hexyloxy)]-2-hydroxy]-phenyl}-6-(4-methoxyphenyl)-1,3,5-triazine ("TINOSORB S" marketed by Ciba), the polymer of N-(2 et 4)-[(2-oxoborn-3-yliden)methyl] benzyl]-acrylamide, 1,4-bisbenzimidazolyl-phenylen-3,3',5,5'-tetrasulfonic acid and salts thereof, the benzalmalonate-substituted polyorganosiloxanes, the benzotriazole-substituted polyorganosiloxanes (Drometrizole Trisiloxane), dispersed 2,2'-methylene-bis-[6-(2H-benzotriazol-2-yl)-4-(1,1,3,3-tetramethylbutyl)phenol] such as that marketed under the trademark MIXXIM BB/100 by Fairmount Chemical, or micronized in dispersed form thereof such as that marketed under the trademark TINOSORB M by Ciba-Geigy, and solubilized 2,2'-methylene-bis-[6-(2H-benzotriazol-2-yl)-4-(methyl)phenol] such as that marketed under the trademark MIXXIM BB/200 by Fairmount Chemical.

Typically preferred among the subject sunscreens are one or more of the following: octyl salicylate, octocrylene, and oxybenzone. Combinations of one of more of these sunscreens is similarly preferred.

The dibenzoyl methane derivatives other than avobenzone are also preferred sunscreens according to the present invention. These are described, for example, in FR-2,326,405, FR-2,440,933 and EP-0,114,607, hereby expressly incorporated by reference.

More preferred dibenzoyl methane sunscreens other than avobenzone include (whether singly or in any combination):

2-methyldibenzoylmethane 4-methyldibenzoylmethane 4-isopropyldibenzoylmethane 4-tert.-butyldibenzoylmethane 2,4-dimethyldibenzoylmethane 2,5-dimethyldibenzoylmethane 4,4'-diisopropyldibenzoylmethane 4,4'-dimethoxydibenzoylmethane 2-methyl-5-isopropyl-4'-methoxydibenzoylmethane 2-methyl-5-tert. -butyl-4'-methoxydibenzoylmethane 2,4-dimethyl-4'-methoxydibenzoylmethane 2,6-dimethyl-4-tert.-butyl-4'-methoxydibenzoylmethane The subject at least one UV-A and/or UV-B sunscreen is advantageously formulated into the compositions of the invention in amounts ranging from about 0.01% to about 10%, and preferably from about 0.1% to about 6%, by weight thereof. Of course, depending upon the nature of the particular formulation, higher or lower amounts may be suitable.

The judiciously selected polymeric film former tricontanyl PVP is also well known to this art and it too is available commercially. Tricontanyl PVP is a copolymer of vinyl pyrrolidone and 1-triacontane. It is marketed in the United States by International Specialty Products ("ISP") under the trademark "Ganex WP-660" and in Europe, also by ISP, under the trademark "Antaron WP-660."

The concentration of the tricontanyl PVP polymer formulated into the compositions of the invention advantageously ranges from about 1% to about 10%, preferably from about 1% to 5%, by weight thereof. Also depending upon the nature of the particular formulation, higher or lower amounts may be suitable.

Thus, the present invention features topically applicable cosmetic/dermatological compositions, and preferably sprayable compositions, comprising both at least one UV-A and/or UV-B sunscreen, notably avobenzone, and tricontanyl PVP, formulated into a topically applicable, cosmetically/dermatologically acceptable vehicle, diluent or carrier therefor.

Concordantly, this invention features a regime or regimen for photoprotecting human skin, hair and/or scalp against the damaging or deleterious effects of ultraviolet irradiation, comprising topically applying onto the skin, hair and/or scalp of a human subject, a cosmetic/dermatological composition which comprises (a) an effective UV-photoprotecting amount of at least one UV-A and/or UV-B sunscreen, most preferably including avobenzone, and (b) an effective SPF-enhancing amount of the copolymer tricontanyl PVP.

In a preferred embodiment of the invention, a regime or regime is featured for photoprotecting human skin, hair and/or scalp against the damaging/deleterious effects of ultraviolet irradiation, particularly solar radiation, comprising spraying onto the skin, hair and/or scalp of a human subject, a sprayable cosmetic/dermatological composition, whether via aerosol or pump system, which comprises (a) an effective UV-photoprotecting amount of at least one UV-A and/or UV-B sunscreen, characteristically including avobenzone, and (b) an effective SPF-enhancing amount of the copolymer tricontanyl PVP.

Also featured are concordantly UV-photoprotecting and artificial or sunless tanning compositions comprising those constituents (a) and (b) as indicated above, together with an effective amount of at least one artificial/sunless tanning agent notably dihydroxyacetone or DHA.

Consistent herewith, in vitro SPF results characteristically ranged from 2–5 and more usually 3–5 times higher than corresponding formulations not containing the tricontanyl PVP polymer. High SPF results were also attained topically applying DHA sunless tanning sprays containing avobenzone/tricontanyl PVP. It too will be appreciated that, other than enhancing SPF values according to the invention, it is also possible to maintain a particular SPF value of a particular composition consistent herewith, for example an SPF value of 15, simply by formulating less of the UV-A and/or UV-B sunscreen. Accordingly, the copolymer tricontanyl PVP serves not only to enhance SPF values, but also, non-quantitatively, to maintain or adjust a particular SPF value while at the same time formulating conspicuously less of the UV filter. Thus, methodology is now available for providing UV-photoprotecting cosmetic/dermatological compositions which comprise at least one UV-A and/or UV-B or avobenzone sunscreen and having a predetermined SPF value, for example an SPF of 15, comprising admixing and intimately formulating an amount of said at least one UV-V and/or UV-B or avobenzone sunscreen less than that required to confer said predetermined SPF value of 15 to said cosmetic/dermatological composition, together with such amount of the copolymer tricontanyl PVP effective to elevate the SPF thereof to said predetermined value of 15.

To date, a wide variety of artificial tanning agents has been developed. Artificial tanners provide the highly sought-after tanning or darkening response once only available through harmful exposure to ultraviolet radiation. DHA, in particular, has been widely utilized in cosmetics to accomplish artificial tanning of the skin. Proteins of the epidermis have a very high concentration of arginine, lysine, and histidine and the reaction of skin with DHA to produce an artificial tan takes advantage of this fact. The tanning reaction proceeds through combination with free amino groups in skin proteins, and particularly by combination of DHA with the free guanido group in arginine.

Preferred among those artificial tanners which are useful in the compositions of the instant invention are those selected from the group comprising: allose, alpha hydroxy substituted ketones such as dihydroxyacetone, altrose, arabinose, erythrose, fructose, galactose, glucose, glyceraldehyde, indoles, lactose, mannose, reose, ribose, pentose, sucrose, tallose, xylose, and mixtures thereof.

Most preferred among these artificial/sunless tanners which are useful in the compositions of the present inventions is dihydroxyacetone. In this respect, it should be appreciated that DHA is not at all easy to formulate, is particulary sensitive and compositions comprised thereof tend to be quite unstable over time (as DHA tolerates but few raw materials, e.g., carbomers). Thus, the stable formulations according to the invention, especially those suited for spray delivery, are all the more unexpected and surprising.

Heretofore, attempts to formulate a high SPF sunscreen spray containing, e.g., avobenzone, met with difficulty; this was due to the incompatibility of avobenzone with other sunscreen filters. To reiterate, it was also difficult to achieve high SPF values in sprayable formulations.

Indeed, high SPF sunscreen sprays are available on the market, but these do not contain avobenzone. High SPF values have thus been obtained by incorporating greater amounts of UV-B absorbing sunscreens such as octylmethoxy cinnamate. However, such formulations provide scant protection against longer wavelength UV-A irradiation.

The compositions of the present invention can be formulated into a wide variety of product types, including creams, dispersions, emulsions (oil-in-water, water-in-oil, water-in-oil-in-water, and oil-in-water-in-silicone), gels, ointments, lotions, milks, mousses, sprays, tonics, and the like.

In a most especially preferred embodiment of the present invention, the subject cosmetic/dermatological compositions are provided as spray delivery systems. This because, heretofore, it was particularly difficult to attain high SPFs with a spray. Also, because of its ease of use, the consumer particularly appreciates a spray delivery system.

The topical cosmetic compositions of the present invention typically comprise a carrier (vehicle or diluent) or mixture of carriers. The carrier should be cosmetically and/or pharmaceutically acceptable, which reflects that the carrier is suitable for topical application onto the skin, has good aesthetic properties, is compatible with the copolymer of the present invention, and any other components, and will not cause any untoward safety or toxicity concerns. The carriers and additional components used to formulate such products vary with the product type and may be routinely chosen by one skilled in the art. The following is a description of some of these carriers and additional components.

The compositions of the present invention can comprise a carrier, or a mixture of carriers, suitable for topical application onto human skin. The carriers typically constitute from about 0.5% to about 99.5% by weight, preferably from about 5.0% to about 99.5% by weight, more preferably from about 10.0% to about 98.0% by weight, of the composition. As used herein, the phrase "suitable for topical application onto human skin" reflects that the carrier does not damage or negatively affect the aesthetics of or cause irritation to human skin.

Carriers suitable for use with the present invention include, for example, those used in the formulation of a wide variety of product types, including creams, dispersions, emulsions, gels, lotions, milks, mousses, sprays, and tonics.

The carriers used herein can include a wide range of components conventionally used in cosmetic/dermatological compositions. The carriers can contain a solvent to dissolve or disperse the polymer. The carriers can also contain a wide variety of additional materials including, but not limited to, esters (such as isopropyl myristate), halogenated hydrocarbons (such as freons), hydrocarbons (such as decene, hexane, and isobutane), linalool, and volatile silicon derivatives (especially siloxanes such as phenyl pentamethyl disiloxane, methoxypropyl heptamethyl cyclotetrasiloxane, chloropropyl pentamethyl disiloxane, hydroxypropyl pentamethyl disiloxane, octamethyl cyclotetrasiloxane, decamethyl cyclopentasiloxane, cyclomethicone, dimethicone), and mixtures thereof.

Mousses and aerosol sprays can also include any of the conventional propellants to deliver the material as a foam, in the case of a mousse, or as a fine, uniform spray, in the case of an aerosol spray. Examples of suitable propellants include materials such as hydrofluorinated compounds, dichlorodifluoromethane, difluoroethane, dimethylether, isobutane, n-butane, propane, or trichlorofluromethane. A tonic or spray product having a low viscosity may also include an emulsifying agent. Examples of suitable emulsifying agents are anionic surfactants, cationic surfactants, nonionic surfactants, and mixtures thereof. Fluorosurfactants are especially preferred, particularly if the product is a preferred spray composition and most especially if it is a spray composition having a relatively low level of volatile organic solvents, such as alcohols, and relatively high levels of water (i.e., in excess of about 10%, by weight, water). If such an emulsifying agent is included, it is preferably present at a level of from about 0.01% to about 7.5% by weight of the composition. The level of propellant can be adjusted as desired, but is generally from about 3% to about 30% by weight of mousse compositions and from about 15% to about 50% by weight of the aerosol spray compositions.

Suitable spray compositions are well known in the art and include conventional, non-aerosol pump sprays, i.e., "atomizers," aerosol containers or cans having propellant, as described above, and also pump aerosol containers utilizing compressed air as the propellant. Pump aerosol containers are disclosed, for example, in U.S. Pat. No. 4,077,441, issued to Olofsson on Mar. 7, 1978, and U.S. Pat. No. 4,850,517, issued to Ter Stege on Jul. 25, 1989, both incorporated herein by reference.

A wide variety of additional components can be employed in the topical cosmetic/dermatological compositions herein. The compositions of the present invention can comprise a safe and effective amount of a pharmaceutical additive or adjuvant. The phrase "safe and effective" connotes an amount of an active agent high enough to significantly or positively modify the condition to be treated, but low enough to avoid serious side effects (at a reasonable benefit/risk ratio) within the scope of sound medical judgment. A safe and effective amount of the pharmaceutical active agent will vary with the specific active species, the ability of the composition to penetrate the active species through the skin, the amount of composition to be applied, the particular condition being treated, the age and physical condition of the patient being treated, the severity of the condition, the duration of the treatment, the nature of concurrent therapy, and like factors.

Useful pharmaceutical active agents which may be conjointly administered according to the present invention include antimicrobial drugs: antibacterials, antifungals, antiprotozoans, and antivirals. Antimicrobial drugs preferred for inclusion in compositions of the present invention comprise pharmaceutically acceptable salts of P-lactam drugs, amanfadine, amikacin, capreomycin, chlorhexidine, chlortetracycline, ciprofloxacin, clindamycin, doxycycline, erythromycin, ethambutol, gentamicin, kanamycin, lineomycin, methacycline, methenamine, metronidazole, miconazole, minocycline, neomycin, netilmicin, norfloxacin, oxytetracycline, paramomycin, pentamidine, quinolone drugs, streptomycin, tetracycline, tobramycin, and triclosan.

The subject cosmetic/dermatological compositions can contain various emulsifiers when formulated as emulsions. These emulsifiers are useful for emulsifying the various carrier components of the compositions herein. Suitable emulsifiers can include any of a wide variety of nonionic, cationic, anionic, and zwitterionic emulsifiers disclosed in the prior patents and other references. See McCutcheon's, *Detergents and Emulsifiers*, North American Edition (1986), published by Allured Publishing Corporation; U.S. Pat. No. 5,011,681, issued to Ciotti et al. on Apr. 30, 1991; U.S. Pat. No. 4,421,769, issued to Dixon et al. on Dec. 20, 1983; and U.S. Pat. No. 3,755,560, issued to Dickert et al. on Aug. 28, 1973. These four publications are incorporated herein by reference in their entirety.

Suitable emulsifier types include acyl lactylates, alkyl phosphates, carboxylic acid copolymers, esters and ethers of glucose, esters of glycerin, esters of propylene glycol, esters of sorbitan anhydrides, esters of sorbitol, ethoxylated ethers, ethoxylated alcohols, fatty acid amides, fatty acid esters of polyethylene glycol, fatty esters of polypropylene glycol, polyoxyethylene fatty ether phosphates, soaps and mixtures thereof.

Preferred emulsifiers can include, but are not limited to, ceteareth-20, ceteth-10, cetyl phosphate, diethanolamine cetyl phosphate, glyceryl stearate, PEG-100 stearate, polyethylene glycol 20 sorbitan monolaurate, polyethylene glycol 5 soya sterol, polysorbate 60, polysorbate 80, potassium cetyl phosphate, PPG-2 methyl glucose ether distearate, steareth-20, and mixtures thereof.

Typically preferred among these emulsifiers which are useful in the compositions of the present inventions is PPG-2 isoceteth-20 acetate (described in U.S. Pat. No. 4,559,226, issued to Fogel et al.).

The subject cosmetic/dermatological compositions can also contain various emollients. Examples of suitable emollients include, but are not limited to, highly branched hydrocarbons, non-polar carboxylic acid and alcohol esters, volatile and non-volatile silicone oils, and mixtures thereof. See, U.S. Pat. No. 4,919,934, issued to Deckner et al. on Apr. 24, 1990, which is incorporated by reference in its entirety.

Typically preferred among these emollients which are useful in the compositions of the present inventions are one or more of the following: octyldodecyl neopentanoate and propylene glycol isoceteth-3 acetate.

A variety of additional components can be incorporated into the subject cosmetic/dermatological compositions. Non-limiting examples of these additional components include cationic polymers and thickeners, chelators, gums and thickeners, low pH thickening agents, polymers for enhancing the film-forming properties and substantivity of the composition, sequestrants, skin penetrating aids, suspending agents, vitamins and derivatives thereof, preservatives and aesthetic components.

Exemplary preservatives, which are conventional in this art and which prevent or retard microbial growth and thus protect cosmetic products from spoilage, are set forth at *CFTA International Cosmetic Ingredient Dictionary and Handbook*, seventh edition, 2, 1654 (1997).

The cosmetic/dermatological compositions of the present invention are administered in conventional fashion to provide the desired benefit. Such methods of use generally involve topical and preferably spray application of an effective amount of the composition onto the skin, which then is allowed to remain until absorbed into or removed from the skin.

Again, enhanced SPF values are provided hereby via the specific addition of the tricontanyl PVP copolymer into the specific sunscreen formulation, for example SPF values greater than 50 and usually even greater than 60. While not wishing to be bound to or by any particular theory, it is believed that the tricontanyl PVP copolymer serves the function of imparting more effectiveness to the at least one UV-A and/or UV-B sunscreen by maintaining a conspicuously thick, continuous sunscreen film over the skin.

Accordingly, high levels of UV-B absorbing filters are not required to attain enhanced SPF values. The subject sunscreen formulations are thus unique in concordantly providing enhanced SPF values and high UV-A photoprotection.

Too, other materials described as film formers have been incorporated into sunscreen formulations. The film former quite usual in this art is PVP/eicosane copolymer; nonetheless, the increase in SPF is not nearly as dramatic as that provided by tricontanyl PVP. Indeed, similar spray formulations containing similar levels of PVP/eicosane copolymer provided average in vitro SPF values of 31, as compared to SPF values of 87 with tricontanyl PVP.

Once again, given that film formers have to date been shown to provide conspicuously modest increases in SPF values, the very high SPF values according to the present invention are most unexpected, especially considering that the subject formulations containing the UV-A filter avobenzone do not contain high levels of UV-B absorbing filters such as octylmethoxy cinnamate.

High SPF-enhancing effects are also provided hereby in formulations containing sunscreens and dihydroxyacetone, formulations that are normally difficult to impart high SPF values thereto.

In order to further illustrate the present invention and the advantages thereof, the following specific examples are given, it being understood that same are intended only as illustrative and in nowise limitative.

In said examples to follow, all parts and percentages are given by weight, unless otherwise indicated.

EXAMPLE 1

The following avobenzone/tricontanyl PVP composition was formulated:

| Phase | Ingredient | % |
|---|---|---|
| A | Water | to 100% |
|   | Humectant | 6 |
|   | Panthenol | 1 |
|   | Preservative | 0.6 |
|   | Thickener/gum | 0.1 |
| B | Avobenzone | 3 |
|   | Octocrylene | 10 |
|   | Oxybenzone | 6 |
|   | Octyl Salicylate | 5 |
|   | Tricontanyl PVP | 3 |
|   | Preservative | 0.8 |
|   | Emulsifier | 2 |
|   | Emollient | 10 |
|   | Emulsifier/thickener | 0.15 |
| C | Silicone Emollient | 4 |
| D | Vitamin E | 0.1 |

The ingredients of Phase A were introduced into a main tank and heated with homogenization to 80°–85° C. The ingredients of Phase B were intimately admixed in a separate tank ("side tank") and heated with moderate propeller mixing. Once the temperature of the contents of both tanks was 80°–85° C. and homogeneous, the content of the side tank were added to the main tank. The entire contents of the main tank were mixed with increased homogenization for 15 to 20 minutes. Cooling was initiated and homogenization was decreased. Once the contents of the main tank attained a temperature of 35° C., the contents of Phases C and D were added to the main tank. Once the contents of the main tank reached 25° C., homogenization and cooling were ceased.

EXAMPLE 2

A concordantly UV-photoprotecting and artificial/sunless tanning composition was formulated by duplicating that of Example 1, but including up to 7.5% of dihydroxyacetone in Phase A.

EXAMPLE 3

Efficacy of Various Compositions as Determined by In Vitro SPF Utilizing Optometrics SPF 290 Apparatus

| Description of Formulation | In Vitro SPF | Standard Deviation | % Change over Base Formulation |
|---|---|---|---|
| Base formulation (no polymer) | 22.4 | 2.46 | — |
| Base + 3% PVP/Eicosane Copolymer | 30.9 | 5.22 | 37.9 |
| Base + 3% Tricontanyl PVP (according to invention) | 86.0 | 12.2 | 283.9 |

EXAMPLE 4

In this example, concordantly UV-photoprotecting and artificial/sunless tanning compositions were formulated containing avobenzone in combination with dihydroxyacetone, and the respective SPFs were measured.

The following results were obtained:

| Description of Formulation | In Vitro SPF | Standard Deviation | % Change over Base Formulation |
|---|---|---|---|
| Base + 5% DHA (no polymer) | 18.7 | 1.48 | — |
| Base + 5% DHA + 3% Tricontanyl PVP (according to invention) | 64.6 | 28.6 | 245.4 |

It will thus be seen that the formulation according to the invention provided both high SPF protection and a natural tan, normally difficult to obtain. However, high SPF values were provided when the tricontanyl PVP was incorporated into the formulation.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A regime/regimen for improvedly UV-photoprotecting human skin, hair and/or scalp against the deleterious effects of ultraviolet irradiation, comprising topically applying thereon (a) an effective UV-photoprotecting amount of at least one UV-A and/or UV-B sunscreen and (b) an amount of the copolymer tricontanyl PVP effective to significantly enhance the SPF value of said at least one UV-A and/or UV-B sunscreen, formulated into (c) a topically applicable, cosmetically/dermatologically acceptable vehicle, diluent or carrier therefor.

2. A regime/regimen for improvedly UV-photoprotecting human skin, hair and/or scalp against the deleterious effects of ultraviolet irradiation, comprising topically applying thereon (a) an effective UV-photoprotecting amount of the sunscreen avobenzone and (b) an amount of the copolymer tricontanyl PVP effective to significantly enhance the SPF value of said avobenzone sunscreen, formulated into (c) a topically applicable, cosmetically/dermatologically acceptable vehicle, diluent or carrier therefor.

3. The UV-photoprotecting regime/regimen as defined by claims 1 or 2, the amount of said copolymer tricontanyl PVP being effective to enhance the SPF value of said at least one UV-A and/or UV-B or avobenzone sunscreen from 2–5 times higher.

4. The UV-photoprotecting regime/regimen as defined by claims 1 or 2, comprising topically applying such amounts of said at least one UV-A and/or UV-B or avobenzone sunscreen and said copolymer tricontanyl PVP as to provide an SPF value of greater than 50.

5. The UV-photoprotecting regime/regimen as defined by claims 1 or 2, comprising topically applying such amounts of said at least one UV-A and/or UV-B or avobenzone sunscreen and said copolymer tricontanyl PVP as to provide an SPF value of greater than 60.

6. A regime/regimen for improvedly UV-photoprotecting human skin, hair and/or scalp against the deleterious effects of ultraviolet irradiation, comprising topically spraying thereon (a) an effective UV-photoprotecting amount of at least one UV-A and/or UV-B sunscreen and (b) an amount of the copolymer tricontanyl PVP effective to significantly enhance the SPF value of said at least one UV-A and/or UV-B sunscreen, formulated into (c) a topically and sprayable applicable, cosmetically/dermatologically acceptable vehicle, diluent or carrier therefor.

7. A regime/regimen for improvedly UV-photoprotecting human skin, hair and/or scalp against the deleterious effects of ultraviolet irradiation, comprising topically spraying thereon (a) an effective UV-photoprotecting amount of the sunscreen avobenzone and (b) an amount of the copolymer tricontanyl PVP effective to significantly enhance the SPF value of said avobenzone sunscreen, formulated into (c) a topically and sprayable applicable, cosmetically/dermatologically acceptable vehicle, diluent or carrier therefor.

8. The UV-photoprotecting spray regime/regimen as defined by claims 6 or 7, the amount of said copolymer tricontanyl PVP being effective to enhance the SPF value of said at least one UV-A and/or UV-B or avobenzone sunscreen from 2–5 times higher.

9. The UV-photoprotecting spray regime/regimen as defined by claims 6 or 7, comprising topically spray applying such amounts of said at least one UV-A and/or UV-B or avobenzone sunscreen and said copolymer tricontanyl PVP as to provide an SPF value of greater than 50.

10. The UV-photoprotecting spray regime/regimen as defined by claims 6 or 7, comprising topically spray applying such amounts of said at least one UV-A and/or UV-B or avobenzone sunscreen and said copolymer tricontanyl PVP as to provide an SPF value of greater than 60.

11. A regime/regimen for concordantly artificially/sunless tanning and improvedly UV-photoprotecting human skin, hair and/or scalp against the deleterious effects of ultraviolet irradiation, comprising topically applying thereon (a) an effective UV-photoprotecting amount of at least one UV-A and/or UV-B sunscreen, (b) an amount of the copolymer tricontanyl PVP effective to significantly enhance the SPF value of said at least one UV-A and/or UV-B sunscreen and (c) an effective artificial tanning amount of at least one artificial tanning agent, formulated into (d) a topically applicable, cosmetically/dermatologically acceptable vehicle, diluent or carrier therefor.

12. A regime/regimen for concordantly artificially/sunless tanning and improvedly UV-photoprotecting human skin, hair and/or scalp against the deleterious effects of ultraviolet irradiation, comprising topically spraying thereon (a) an effective UV-photoprotecting amount of the sunscreen avobenzone, (b) an amount of the copolymer tricontanyl PVP effective to significantly enhance the SPF value of said avobenzone sunscreen and (c) an effective artificial tanning amount of at least one artificial tanning agent, formulated into (d) a topically applicable, cosmetically/dermatologically acceptable vehicle, diluent or carrier therefor.

13. The concordantly artificially/sunless tanning and UV-photoprotecting regime/regimen as defined by claims 11 or 12, said at least one artificial tanning agent comprising dihydroxyacetone.

14. A regime/regimen for concordantly artificially/sunless tanning and improvedly UV-photoprotecting human skin, hair and/or scalp against the deleterious effects of ultraviolet irradiation, comprising topically spraying thereon (a) an effective UV-photoprotecting amount of at least one UV-A and/or UV-B sunscreen, (b) an amount of the copolymer tricontanyl PVP effective to significantly enhance the SPF value of said at least one UV-A and/or UV-B sunscreen and (c) an effective artificial tanning amount of at least one artificial tanning agent, formulated into (d) a topically and sprayable applicable, cosmetically/dermatologically acceptable vehicle, diluent or carrier therefor.

15. A regime/regimen for concordantly artificially/sunless tanning and improvedly UV-photoprotecting human skin, hair and/or scalp against the deleterious effects of ultraviolet irradiation, comprising topically spraying thereon (a) an effective UV-photoprotecting amount of the sunscreen avobenzone, (b) an amount of the copolymer tricontanyl PVP effective to significantly enhance the SPF value of said avobenzone sunscreen and (c) an effective artificial tanning amount of at least one artificial tanning agent, formulated into (d) a topically and sprayable applicable, cosmetically/dermatologically acceptable vehicle, diluent or carrier therefor.

16. The concordantly artificially/sunless tanning and improvedly UV-photoprotecting regime/regimen as defined by claims 14 or 15, said at least one artificial tanning agent comprising dihydroxyacetone.

17. A topically applicable cosmetic/dermatological composition suited for improvedly UV-photoprotecting human skin, hair and/or scalp against the deleterious effects of ultraviolet irradiation, comprising (a) an effective UV-photoprotecting amount of at least one UV-A and/or UV-B sunscreen and (b) an amount of the copolymer tricontanyl PVP effective to significantly enhance the SPF value of said at least one UV-A and/or UV-B sunscreen, formulated into (c) a topically applicable, cosmetically/dermatologically acceptable vehicle, diluent or carrier therefor.

18. A topically applicable cosmetic/dermatological composition suited for improvedly UV-photoprotecting human skin, hair and/or scalp against the deleterious effects of ultraviolet irradiation, comprising (a) an effective UV-photoprotecting amount of the sunscreen avobenzone and (b) an amount of the copolymer tricontanyl PVP effective to significantly enhance the SPF value of said avobenzone sunscreen, formulated into (c) a topically applicable, cosmetically/dermatologically acceptable vehicle, diluent or carrier therefor.

19. The cosmetic/dermatological UV-photoprotecting composition as defined by claims 17 or 18, the amount of said copolymer tricontanyl PVP being effective to enhance the SPF value of said at least one UV-A and/or UV-B or avobenzone sunscreen from 2–5 times higher.

20. An aerosol or pump system adapted for spray-delivery and confining a topically applicable cosmetic/dermatological composition suited for improvedly UV-photoprotecting human skin, hair and/or scalp against the deleterious effects of ultraviolet irradiation, comprising (a) an effective UV-photoprotecting amount of at least one UV-A and/or UV-B sunscreen and (b) an amount of the copolymer tricontanyl PVP effective to significantly enhance the SPF value of said at least one UV-A and/or UV-B sunscreen, formulated into (c) a topically and sprayable applicable, cosmetically/dermatologically acceptable vehicle, diluent or carrier therefor.

21. An aerosol or pump system adapted for spray-delivery and confining a topically applicable cosmetic/dermatological composition suited for improvedly UV-photoprotecting human skin, hair and/or scalp against the deleterious effects of ultraviolet irradiation, comprising (a) an effective UV-photoprotecting amount of the sunscreen avobenzone and (b) an amount of the copolymer tricontanyl PVP effective to significantly enhance the SPF value of said avobenzone sunscreen, formulated into (c) a topically and sprayable applicable, cosmetically/dermatologically acceptable vehicle, diluent or carrier therefor.

22. The aerosol or pump system as defined by claims 20 or 21, the amount of said tricontanyl PVP copolymer being effective to enhance the SPF value of said at least one UV-A and/or UV-B or avobenzone sunscreen from 2–5 times higher.

23. A topically applicable cosmetic/dermatological composition suited for concordantly artificially/sunless tanning and improvedly UV-photoprotecting human skin, hair and/or scalp against the deleterious effects of ultraviolet irradiation, comprising (a) an effective UV-photoprotecting amount of at least one UV-A and/or UV-B sunscreen, (b) an amount of the copolymer tricontanyl PVP effective to significantly enhance the SPF value of said at least one UV-A and/or UV-B sunscreen and (c) an effective amount of at least one artificial tanning agent, formulated into (d) a topically applicable, cosmetically/dermatologically acceptable vehicle, diluent or carrier therefor.

24. A topically applicable cosmetic/dermatological composition suited for concordantly artificially/sunless tanning and improvedly UV-photoprotecting human skin, hair and/or scalp against the deleterious effects of ultraviolet irradiation, comprising (a) an effective UV-photoprotecting amount of the sunscreen avobenzone, (b) an amount of the copolymer tricontanyl PVP effective to significantly enhance the SPF value of said avobenzone sunscreen and (c) an effective amount of at least one artificial tanning agent, formulated into (d) a topically applicable, cosmetically/dermatologically acceptable vehicle, diluent or carrier therefor.

25. The concordantly artificially/sunless tanning and improvedly UV-photoprotecting cosmetic/dermatological composition as defined by claims 23 or 24, said at least one artificial tanning agent comprising dihydroxyacetone.

26. An aerosol or pump system adapted for spray-delivery and confining a topically applicable cosmetic/dermatological composition suited for concordantly artificially/sunless tanning and improvedly UV-photoprotecting human skin, hair and/or scalp against the deleterious effects of ultraviolet irradiation, comprising (a) an effective UV-photoprotecting amount of at least one UV-A and/or UV-B sunscreen, (b) an amount of the copolymer tricontanyl PVP effective to significantly enhance the SPF value of said at least one UV-A and/or UV-B sunscreen and (c) an effective amount of at least one artificial tanning agent, formulated into (d) a topically and sprayable applicable, cosmetically/dermatologically acceptable vehicle, diluent or carrier therefor.

27. An aerosol or pump system adapted for spray-delivery and confining a topically applicable cosmetic/dermatological composition suited for concordantly artificially/sunless tanning and improvedly UV-photoprotecting human skin, hair and/or scalp against the deleterious effects of ultraviolet irradiation, comprising (a) an effective UV-photoprotecting amount of the sunscreen avobenzone, (b) an amount of the copolymer tricontanyl PVP effective to significantly enhance the SPF value of said avobenzone sunscreen and (c) an effective amount of at least one artificial tanning agent, formulated into (d) a topically and sprayable applicable, cosmetically/dermatologically acceptable vehicle, diluent or carrier therefor.

28. The aerosol or pump system as defined by claims 26 or 27, said at least one artificial tanning agent comprising dihydroxyacetone.

29. A method for enhancing the SPF-value of at least one UV-A and/or UV-B sunscreen in UV-photoprotecting cosmetic/dermatological compositions comprised thereof, which comprises admixing and intimately formulating therewith an amount of the copolymer tricontanyl PVP effective to significantly enhance the SPF value of said at least one UV-A and/or UV-B sunscreen.

30. A method for enhancing the SPF-value of the sunscreen avobenzone in UV-photoprotecting cosmetic/dermatological compositions comprised thereof, which comprises admixing and intimately formulating therewith an amount of the copolymer tricontanyl PVP effective to significantly enhance the SPF value of said avobenzone sunscreen.

31. A method for providing a UV-photoprotecting cosmetic/dermatological composition which comprises at least one UV-A and/or UV-B sunscreen and having a predetermined SPF value, comprising admixing and intimately formulating an amount of said at least one UV-A and/or UV-B sunscreen less than that required to confer said predetermined SPF value to said cosmetic/dermatological composition, together with such amount of the copolymer tricontanyl PVP effective to elevate the SPF thereof to said predetermined value.

32. A method for providing a UV-photoprotecting cosmetic/dermatological composition which comprises the sunscreen avobenzone and having a predetermined SPF value, comprising admixing and intimately formulating an amount of said sunscreen avobenzone less than that required to confer said predetermined SPF value to said cosmetic/dermatological composition, together with such amount of the copolymer tricontanyl PVP effective to elevate the SPF thereof to said predetermined value.

* * * * *